(12) United States Patent
Piecuch

(10) Patent No.: US 11,259,932 B2
(45) Date of Patent: Mar. 1, 2022

(54) ADDITIVE MANUFACTURED FEMORAL COMPONENTS

(71) Applicant: Zimmer, Inc., Warsaw, IN (US)

(72) Inventor: Cristina Piecuch, Winona Lake, IN (US)

(73) Assignee: Zimmer, Inc., Warsaw, IN (US)

( * ) Notice: Subject to any disclaimer, the term of this patent is extended or adjusted under 35 U.S.C. 154(b) by 282 days.

(21) Appl. No.: 15/846,304

(22) Filed: Dec. 19, 2017

(65) Prior Publication Data

US 2018/0228616 A1 Aug. 16, 2018

Related U.S. Application Data

(60) Provisional application No. 62/457,327, filed on Feb. 10, 2017.

(51) Int. Cl.
| | | |
|---|---|---|
| *A61F 2/32* | (2006.01) | |
| *A61F 2/36* | (2006.01) | |
| *A61F 2/30* | (2006.01) | |
| *B22F 5/00* | (2006.01) | |
| *B22F 7/00* | (2006.01) | |
| *B33Y 80/00* | (2015.01) | |
| *B33Y 10/00* | (2015.01) | |
| *B22F 7/06* | (2006.01) | |
| *B22F 10/20* | (2021.01) | |

(52) U.S. Cl.
CPC ........ *A61F 2/3662* (2013.01); *A61F 2/30942* (2013.01); *B22F 5/00* (2013.01); *B22F 7/004* (2013.01); *B22F 7/06* (2013.01); *B22F 10/20* (2021.01); *B33Y 10/00* (2014.12); *B33Y 80/00* (2014.12); *A61F 2002/30011* (2013.01); *A61F 2002/30014* (2013.01); *A61F 2002/3092* (2013.01); *A61F 2002/30113* (2013.01); *A61F 2002/30158* (2013.01); *A61F 2002/30884* (2013.01); *A61F 2002/30962* (2013.01); *A61F 2002/30985* (2013.01); *A61F 2002/3678* (2013.01)

(58) Field of Classification Search
CPC combination set(s) only.
See application file for complete search history.

(56) References Cited

U.S. PATENT DOCUMENTS

| | | | | |
|---|---|---|---|---|
| 3,905,777 | A * | 9/1975 | Lacroix ..................... | A61F 2/28 428/550 |
| 2006/0184250 | A1 * | 8/2006 | Bandoh ..................... | A61F 2/36 623/23.32 |
| 2007/0116734 | A1 * | 5/2007 | Akash ..................... | A61L 27/56 424/423 |

* cited by examiner

*Primary Examiner* — Christopher D. Prone
(74) *Attorney, Agent, or Firm* — Schwegman Lundberg & Woessner, P.A.

(57) ABSTRACT

Described is a femoral component of a prosthetic hip implant. The femoral component can include: a neck portion; and a stem portion including a proximal end and a distal end. The neck portion extends from the proximal end, and the stem portion comprises a first solid portion and at least one additional portion including at least one of a hollow portion, a porous portion, and a second solid portion comprised of a different solid material from a solid material of the first solid portion. The first solid portion and the at least one additional portion are in a predetermined configuration. The femoral component comprises a unitary component that is formed by additive manufacturing of the femoral component from a 3D model of the femoral component.

11 Claims, 4 Drawing Sheets

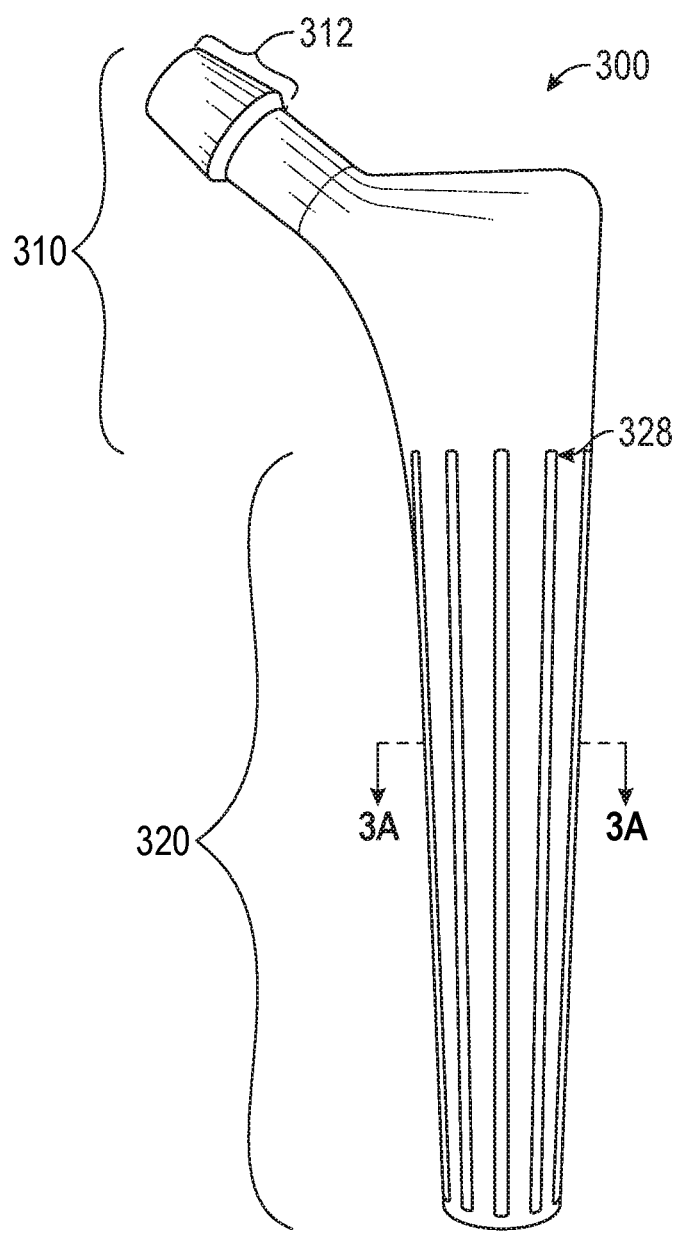
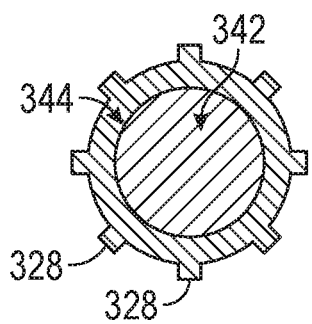
FIG. 3A
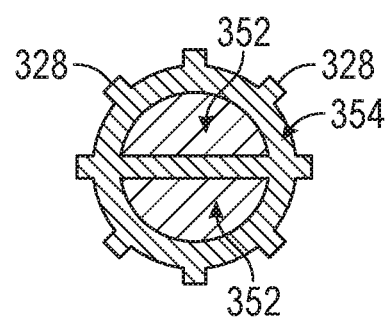
FIG. 3B
FIG. 3

ADDITIVE MANUFACTURED FEMORAL COMPONENTS

CLAIM OF PRIORITY

This patent application claims the benefit of priority, under 35 U.S.C. Section 119(e), to Cristina Piecuch, U.S. Patent Application Ser. No. 62/457,327, entitled "ADDITIVE MANUFACTURED FEMORAL COMPONENT," filed on Feb. 10, 2017, each of which is hereby incorporated by reference herein in its entirety.

TECHNICAL FIELD

The present subject matter relates generally to orthopedic implants and methods of manufacturing an orthopedic implant. In particular, the present disclosure relates to a femoral component of a hip implant that is manufactured by an additive manufacturing process.

BACKGROUND

Artificial implants, including hip joints, shoulder joints, and knee joints, are widely used in orthopedic surgery. Artificial hip and shoulder joints are generally ball and socket joints, designed to match as closely as possible the function of the natural joint. To duplicate a joint's natural action, a total joint replacement implant has three parts: a stem component, which fits into the femur or humerus and provides stability; a ball component, which replaces the spherical head of the femur or humerus; and a cup component, which replaces the worn-out hip or shoulder socket.

There are many types of stem components that can be used in joint replacement surgery to secure the artificial ball that will articulate with the artificial socket or cup. Some stem components are modular, allowing a greater range of options during the surgery. Each component comes in various sizes in order to accommodate various body sizes and types. In some designs, the stem and ball are one piece; in other designs, they may be provided as separate pieces. In further designs, the stem and ball components can feature a modular body, a removable neck, or any combination of these or additional features. Such designs and their combinations will be referred to throughout this document as "modular," and are intended to allow for additional customization and fit.

Specifically, modular stem components may be provided in any number of lengths and widths. Corresponding modular bodies, necks and balls can be provided in various sizes, allowing the surgeon to select the best options for a particular patient. Other stem components may be non-modular, and may provide a stem, neck, and ball in a one-piece configuration.

OVERVIEW

In the realm of orthopedic surgery, it is known to use implants to fix the position of bones. In this way, bones can be reconstructed, and malformations or other injuries corrected. However, different bones within the body have different functions and are exposed to different forces and stresses. Consequently, a single type of orthopedic implant is not well suited for implanting into the various types of bones which experience different forces and stresses, nor into different patients that may have different needs.

Orthopedic implant design is complicated by large bending stiffness (or flexural rigidity) of the implant, which is at least 10 times greater than cortical bone. Effects of a stiffness mismatch between the implant and bone have been extensively studied relating to total hip arthroplasty (THA). Clinical experience has shown that the stiffness mismatch is a primary cause of accelerated bone resorption due to stress shielding. This response to sub-optimal bone loading can lead to loss of proximal support, implant subsidence, potential bone fracture, possible fatigue fracture of the implant, and, most importantly, reduction of bone stock that jeopardizes the outcome of any future revision surgery.

The present inventor has recognized the need for orthopedic implants that can have physical properties that are varied and are capable of addressing differing types of forces and stresses on the implants. Particularly, a need to individualize such an implant for each particular patient is recognized by the inventor.

Additive manufacturing is a name used to describe technologies that build three-dimensional (3D) objects by adding layer-upon-layer of material. The material can be a plastic, a metal, concrete, etc. It is common to use 3D modeling software (Computer Aided Design or CAD) in order to provide a sketch or plan, which is followed by a machine or other equipment that lays down successive layers of material to fabricate a 3D object.

The present inventor has recognized, among other things, that additive manufacturing can be used to fabricate orthopedic implants, and particularly specialized or custom orthopedic implants that address certain anatomies or issues, such as stress shielding. A benefit of using such additive manufacturing of orthopedic implants is that the entire implant can be made using a single unit operation fabrication for manufacturing complete parts of various configurations having both a solid portion and a porous and/or hollow portion. Also, the location and configuration of the porous (or hollow) and solid portions can be customized to address certain anatomies and to address stress shielding while maintaining fatigue performance of the device, for example. Another benefit of the manufacturing process is that there are reduced manufacturing costs compared to specialized and conventional manufacturing methods. The lower costs result from lower set up costs and economies of scale associated with additive manufacturing one-off components. A further benefit is that custom implants can be designed based on the anatomy and desired joint articulation of specific patients, which would not be possible with conventional manufacturing processes.

This overview is intended to provide an overview of subject matter of the present patent application. It is not intended to provide an exclusive or exhaustive explanation of the present subject matter. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 3 shows a side view of a femoral component of a hip joint endoprosthesis in accordance with at least one example of the present disclosure;

FIG. 3A shows a cross-section through the femoral component of FIG. 3 along line 3A-3A in accordance with at least one example of the present disclosure; and FIG. 3B shows another cross-section through the femoral component of FIG. 3 along line 3A-3A in accordance with at least one example of the present disclosure.

DETAILED DESCRIPTION

With reference to the human body and components of the system described herein which are intended to be implanted in the human body, the terms "proximal" and "distal" are defined in reference to the location at which a limb is connected to the torso, with the term "proximal" being the end of the limb, bone or plate closer to the torso, and the term "distal" being the end of the limb, bone or plate further from the torso. In addition, the term "lower" and "upper" in reference to plate surfaces are designations in which the lower surface is that surface closer to or seating on the bone and the upper surface is that surface opposite the lower surface.

The present disclosure relates to an orthopedic implant. In particular, the present disclosure relates to a prosthetic hip implant, including a femoral component comprising: a neck portion; and a stem portion including a proximal end and a distal end, wherein the neck portion extends from the proximal end, and the stem portion comprises at least one solid portion and at least one hollow or porous portion in a predetermined configuration; wherein the femoral component is formed by additive manufacturing of the femoral component from a 3D model of the femoral component based upon an intended implantation position of the femoral component in a bone of a patient. The femoral component can be manufactured by additive manufacturing of the entire part, inclusive of its solid and porous (or hollow) portions. Any additive manufacturing process can be used to make the implant, including direct metal laser sintering (DMLS), selective laser sintering, and electron beam melting, for example.

Figure 1:
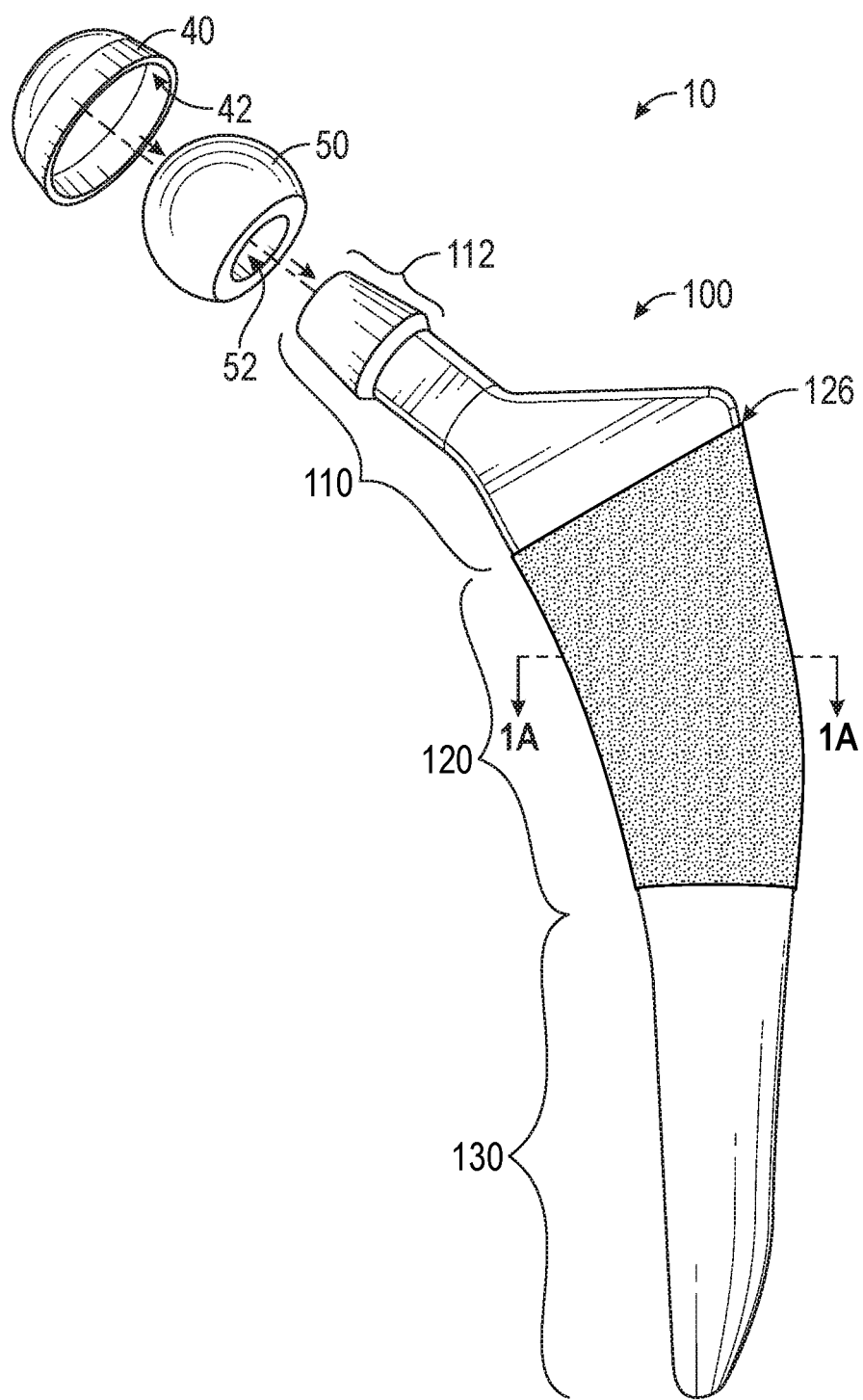
FIG. 1 shows a side view of a femoral component and other components of a hip joint endoprosthesis in accordance with at least one example of the present disclosure.

Referring to FIG. 1, a hip implant 10 is shown according to an example of the present disclosure. Implant 10, including all of its components, can be constructed of a biocompatible material such as titanium, titanium alloy, cobalt chrome, stainless steel, magnesium, niobium, tantalum, etc., and composites thereof, or other metals, polymers or alloys suitable for a hip prosthesis. Implant 10 can comprise three primary components, which can include an acetabular component 40, a femoral ball 50, and a femoral component 100. The femoral component 100 can fit in or attach to the femoral ball 50. The femoral ball 50 can then rest inside recess 42 of acetabular component 40, which can be implanted into a hip of a patient. Femoral ball 50 can rotate within recess 42 of the acetabular component 40. Femoral ball 50 can be spherically-shaped, as shown, or, alternatively, can have other suitable shapes, which can include flattened portions. The acetabular component 40 can be a monoblock or can be modular. The femoral ball 50 in this disclosure is not limited to the specific example shown in FIG. 1, and can encompass all suitable femoral ball designs known in the art. Similarly, the acetabular component is not limited to the specific example shown in FIG. 1 but can include all suitable acetabular component designs known in the art.

The femoral component 100 can be formed as a unitary body or component, or alternatively can be formed as a multi-part component with the multiple parts assembled together. Regardless of whether the femoral component 100 is formed as a unitary body/component or a multi-part component, it can be divided into at least three portions for description purposes that can vary in purpose, composition and shape, for example. A first section can be a neck section 110 that is a proximal-most portion of the femoral component 100 and that can function to connect the femoral component 100 to the femoral ball 50. The neck section 110 can have a proximal end 112 that can have a short cylindrical configuration and can have a slight taper. This proximal end 112 can be configured to be received in a correspondingly shaped and sized cylindrical recess 52 in the femoral ball 50. Together, proximal end 112 and recess 52 can form a Morse taper connection, for example.

A second section of the femoral component 100 can be a middle section 120. The middle section 120 can have an elongated tapering shape that extends distally between the neck section 110 and a distal section 130, which is a third section of the femoral component 100. Alternatively, however, the middle section may not be tapered and could have a more uniform width. The middle section 120 can have a trapezoidal-shaped cross-section, although other shapes are also contemplated.

Other styles, shapes and configurations of the femoral component are contemplated, besides those shown and described herein. For example, the femoral component can also be one of the following: an uncemented tapered wedge component (e.g., having a blade, a trapezoidal or a square cross-section) with a proximal porous coating on only proximal macro features for fixation (e.g., having no porous coating, but one that can be possibly grit blasted); an uncemented fit and fill component (e.g., having a tapered round cross-section with porous coating on proximal ⅔ of component, a tapered round cross-section with splines and no porous coating, a fully cylindrical cross-section with porous coating along its full or partial length, or a fully cylindrical cross-section with no porous coating); and a cemented component (e.g., having an oval cross-section or rectangular cross-section, which is typically tapered along its length). The examples of femoral components shown and described in the present disclosure are examples, and any other suitable types of femoral components are also contemplated.

In particular, the femoral component 100 in FIG. 1 is considered to be a blade style of femoral implant. It is contemplated that the use of the hip implant 10 and style of the hip implant 10 can vary depending upon a particular patient and a particular surgical location in the patient's body. Although the orthopedic implants shown and described herein are generally those that can be used in hip replacement or revision surgeries, other anatomical uses for the subject matter of this disclosure are contemplated, such as for use in implant systems for the lower leg or upper arm, for example.

The neck and distal sections 110, 130 of the femoral component 100 can have solid cross-sections. The middle section 120, however, can have a cross-section that includes both solid, porous and/or hollow components. Solid components of the middle section 120 can be included to withstand fatigue loading in vivo. Internal porous and/or hollow components of the middle section 120 can be included to reduce flexural rigidity and the weight of the stem 100. Porous outer surface features can be included to induce bone ingrowth. The combination of both solid, porous and/or hollow components can allow the stem 100 to be optimized for flexure stiffness to more closely match that of bone and also to minimize stress shielding.

Transitions between the sections 110, 120 and 130 of the stem 100 can be optimally included and located in order to avoid high stress zones in the implant and to meet industry standards. The femoral component 100 can be made using additive manufacturing techniques to have a continuous, integrated structure, including any of the three cross-sections 140, 150 and 160, such as those shown and described herein. However, other suitable cross-sections including solid portions and porous and/or hollow portions are also contemplated.

Figure 1A:
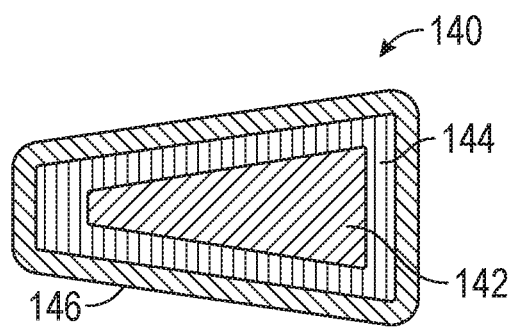
FIG. 1A shows a cross-section through the femoral component of FIG. 1 along line 1A-1A in accordance with at least one example of the present disclosure.
Figure 1B:
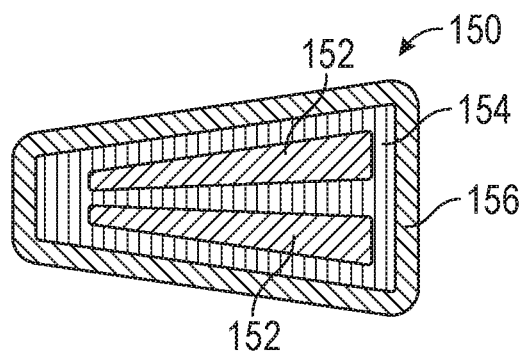
FIG. 1B shows another cross-section through the femoral component of FIG. 1 along line 1A-1A in accordance with at least one example of the present disclosure.
Figure 1C:
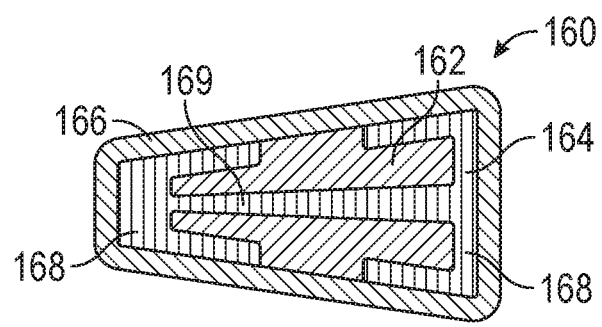
FIG. 1C shows another cross-section through the femoral component of FIG. 1 along line 1A-1A in accordance with at least one example of the present disclosure.

FIGS. 1A, 1B and 1C depict examples of three different cross-sections 140, 150, and 160, respectively, of the middle section 120 of femoral component 100 taken at 1A-1A in FIG. 1. The middle section 120 in all three cross-sections 140, 150 and 160 can have a cross-section having a trapezoidal-shaped profile, as shown. However, other shapes of an outer perimeter or surface of the cross-section are also contemplated by the disclosure, such as, for example, oval-shaped, rectangular-shaped, circular-shaped, or teardrop-shaped. Other suitable shapes are also contemplated, however. The middle section 120 can also include, as shown, a porous outer layer 126 to induce bone ingrowth and/or ongrowth.

A first exemplary cross-section 140 of the middle section 120 of femoral component 100 in FIG. 1, shown in FIG. 1A, can include a core (or longitudinal chamber or aperture) 142 that is porous. By "porous," it is meant that the material is permeated with interconnected interstitial pores. The porous structure can be formed by additive manufacturing using suitable materials, metals or metal alloys known in the art. Alternatively, however, the core 142 can be hollow, or, in other words, the core 142 can be considered to be an aperture. The cross-section 140 can also include a first circumferential solid portion 144 adjacent the core 142. In another example, the core 142 can be formed from a solid material that is different from the solid material of the solid portion 144, which may have a different mechanical property. For example, the mechanical property of strength of the core 142, if it were a solid portion can be less than that of the solid portion 144. Other examples of mechanical properties that can differ in the second solid portion of the core 142 from the solid portion 144 include, but are not limited to, yield strength, compressive strength, fatigue strength, impact strength, deformation, strain, deflection, elasticity, and plasticity, etc.

Further, the cross-section 140 can include a second circumferential porous portion 146 adjacent the first circumferential solid portion 142, and which can serve as an outer surface of the middle section 120. The second circumferential porous portion 146 can be formed by additive manufacturing at the same time as the additive manufacturing of the stem 100, or can be independently manufactured and bonded to the stem 100 by one of the following processes: titanium or titanium alloy plasma spray, sintering of metal beads or metal wire mesh on the stem 100 or diffusion bonding or resistance bonding of trabecular metal pads onto the stem 100 (the additive manufactured porous section 146 and the trabecular metal pads are configured to replace the porous structure of natural bone itself). Thus, the second circumferential porous portion (or outer layer) 146 can promote bone ongrowth and/or ingrowth pending the design of the layer or portion.

The porous structure of the second circumferential porous portion 146, and any other porous portions described herein, can be adapted for the ongrowth and/or ingrowth of cancellous and cortical bone spicules, for example. In an exemplary embodiment, the size and shape of the porous structure can emulate the size and shape of the porous structure of natural bone. Preferably, the average pore diameter of the porous portions described herein, particularly those porous portions that comprise an outer surface of one of the femoral components described herein, can be about 40 μm to about 800 μm with a porosity from about 45% to about 65%. Further, the interconnections between pores can have a diameter larger than about 50-60 microns. In short, the geometric configuration of the porous structure can be configured to encourage natural bone to migrate and grow into the porous structure.

Although specific ranges are given for pore diameters, porosity, and interconnection diameters, these ranges are exemplary and are applicable to one example. In other examples, these ranges could be modified, and the resulting femoral component can still be within the scope of this disclosure.

A second exemplary cross-section 150 of the middle section 120 of femoral component 100, shown in FIG. 1B, can include a solid portion 154 that can include two longitudinal chambers or apertures (if hollow) 152 that are located side-by-side. The two longitudinal chambers 152 can be porous, hollow, or, alternatively, formed of a different solid material (having a different strength, for example) from the solid portion 154. The solid portion 154 can be surrounded by a circumferential porous portion 156 that can make up the outer surface of the middle section 120 of femoral component 100.

A third exemplary cross-section 160 of the middle section 120 of femoral component 100, shown in FIG. 1C, can include a solid portion 164 having generally an I-beam-shape. The I-beam-shaped solid portion 164 can have two flange portions 168 that are connected by a web portion 169. As shown, the two flange portions 168 can be curved to fit the shape of the outer surface or perimeter of middle section 120 as shown, although other shapes are contemplated. Voids can be created in the cross-section 160 by the placement of the I-beam-shaped solid portion 164, which can form two longitudinal chambers or apertures 162. The two longitudinal chambers 162 can be porous, as described herein with regard to the porous core 142 of FIG. 1A, or can be hollow. Alternatively, the chambers can instead be formed from another solid material that differs from the solid material forming the solid portion 164, formed from a metal or polymer for example, which can have a different strength, for example. A porous portion 166 can surround the I-beam shaped solid portion 164 and the two longitudinal chambers 162 (whether porous, hollow or a solid), and can comprise the outer surface of the middle section 120.

Figure 2:
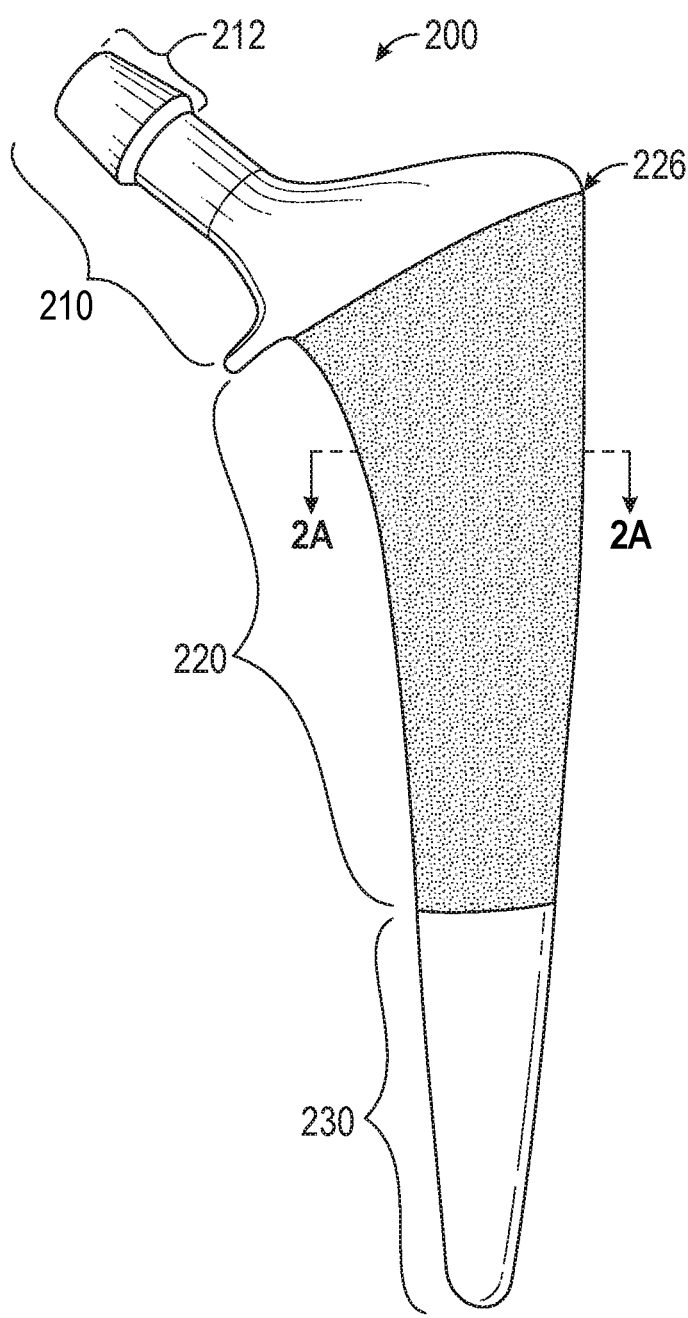
FIG. 2 shows a side view of a femoral component of a hip joint endoprosthesis in accordance with at least one example of the present disclosure.

FIG. 2 shows a side view of another example of a femoral component 200 in accordance with the present disclosure. In particular, the femoral component 200 in FIG. 2 is considered to be a cylindrical-stemmed implant. The femoral component 200 can be formed as a unitary body or component, or alternatively can be formed as a multi-part component with the multiple parts assembled together. Regardless of whether the femoral component 200 is formed as a unitary body/component or a multi-part component, it can be divided into at least three portions for description purposes that can vary in purpose, composition and shape, for example. A first section can be a neck section 210 that is a proximal-most section of the femoral component 200 and that can function to connect the femoral component 200 to a femoral ball (not shown). The neck section 210 can have a proximal end 212 that can have a short cylindrical configuration and can have a slight taper. This proximal end 212 can be configured to be received in a correspondingly shaped and sized cylindrical recess in a femoral ball (not shown).

A second section of the femoral component 200 can be a middle section 220. The middle section 220 can have an elongated cylindrical tapering shape that extends distally between the neck section 210 and a distal section 230, which is a third section, of the femoral component 200.

The neck and distal sections 210, 230 of the femoral component 200 can have solid cross-sections. The middle section 120, however, can have a cross-section that includes both solid and porous (or hollow) components. Solid components of the middle section 220 can be included to withstand fatigue loading in vivo. The porous or hollow components of the middle section 220 can be included to reduce flexural rigidity and the weight of the stem 200, as well as to induce bone ingrowth, if the outer surface is porous. The combination of both solid and porous (or hollow) components can allow the stem 200 to be optimized for flexure stiffness to more closely match that of bone and also to minimize stress shielding.

Transitions between the sections 210, 220 and 230 of the stem 200 can be optimally included and located in order to avoid high stress zones in the implant and to meet industry standards. The femoral component 200 can be made using additive manufacturing techniques to have a continuous, integrated structure, including, for example, either of the two cross-sections 240 and 250, such as those shown and described herein. Other suitable cross-sections are also contemplated, however.

Figure 2A:
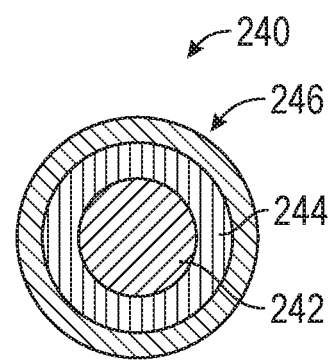
FIG. 2A shows a cross-section through the femoral component of FIG. 2 along line 2A-2A in accordance with at least one example of the present disclosure.
Figure 2B:
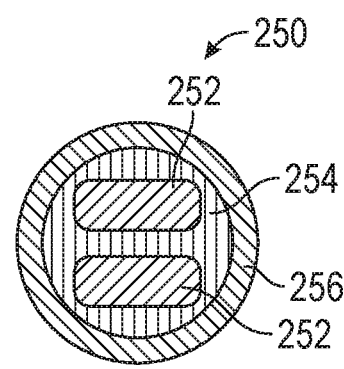
FIG. 2B shows another cross-section through the femoral component of FIG. 2 along line 2A-2A in accordance with at least one example of the present disclosure.

FIGS. 2A and 2B include two different exemplary cross-sections 240 and 250, respectively, of the middle section 220 of femoral component 200 taken at 2A-2A in FIG. 2, for example. The middle section 220 in both cross-sections 240 and 250 can have a cross-section having a circular-shaped profile, as shown. However, other shapes of an outer perimeter or surface of the cross-section are also contemplated by the disclosure. The middle section 220 also includes, as shown, a porous outer layer 226.

The first exemplary cross-section 240 of the middle section 220 of femoral component 200 in FIG. 2, shown in FIG. 2A, can include a core (or longitudinal chamber) 242 that is porous. The porous structure can be formed by additive manufacturing at the same time as the solid internal geometry 244 or 254. Alternatively, however, the core 242 can be hollow (in other words, can be an aperture) or can be made of a solid material that is different (such as having a different strength) from a solid material used in another portion of the middle section 220. The cross-section 240 can include a first circumferential solid portion 244 adjacent the core 242.

In another example, the core 242 can be formed from a solid material that is different from the solid material of the solid portion 144, which can have a different mechanical property. For example, the mechanical property of strength of the core 242, if it were a solid portion can be less than that of the solid portion 244. Other examples of mechanical properties that can differ in the second solid portion of the core 242 from the solid portion 244 include, but are not limited to, yield strength, compressive strength, fatigue strength, impact strength, deformation, strain, deflection, elasticity, and plasticity, etc.

Further, the cross-section 240 can include a second circumferential porous portion 246 adjacent the first circumferential solid portion 242, and which serves as an outer surface of the middle section 220. The second circumferential porous portion 246 can be formed by additive manufacturing at the same time as the solid sections 244, or can be independently manufactured and bonded to the stem 200 by one of the following processes: titanium or titanium alloy plasma spray, sintering of metal beads or metal wire mesh onto the stem 200 or diffusion bonding or resistance bonding of trabecular metal pads onto the stem 200 (the additive manufactured porous section 246 and trabecular metal pads are configured to replicate the porous structure of natural bone itself). Thus, the second circumferential porous portion (or outer layer) 246 can promote bone ongrowth and/or ingrowth pending the design of the layer.

The second exemplary cross-section 250 of the middle section 220 of femoral component 200, shown in FIG. 2B, can include a solid portion 254 that includes two longitudinal chambers or apertures 252 that are located side-by-side. The two longitudinal chambers 252 can be porous or, alternatively, can be hollow (or, in other words, can be apertures) or made of a solid material that differs from another solid portion (such as 254) of middle section 220. The solid portion 254 can be surrounded by a circumferential porous portion 256 that can make up the outer surface of the middle portion 220 of femoral component 200.

FIG. 3 shows a side view of another example of a femoral component 300 in accordance with the present disclosure. In particular, the femoral component 300 in FIG. 3 is considered to have a cylindrical tapered, fluted stem. The femoral component 300 can be formed as a unitary body or component, or alternatively can be formed as a multi-part component with the multiple parts assembled together. Regardless of whether the femoral component 300 is formed as a unitary body/component or a multi-part component, it can be divided into at least two portions for description purposes that can vary in purpose, composition and shape, for example. A first section can be a neck section 310 that is a proximal-most portion of the femoral component 300 and that can function to connect the femoral component 300 to a femoral ball (not shown). The neck section 310 can have a proximal end 312 that can have a short cylindrical configuration and can have a slight taper. This proximal end 312 can be configured to be received in a correspondingly shaped and sized cylindrical recess in a femoral ball (not shown).

A second section of the femoral component 200 can be a stem section 320. The stem section 220 can have an elongated tapering shape that extends distally from the neck section of the femoral component 300. The stem section 320 can include a plurality of longitudinally extending flutes 328 along an incremental length of the outer surface thereof.

Sharp edges on the flutes 328 can dig into a cortical bone wall of an intramedullary canal in a bone, for example, and can increase torsional stability of the stem section 320 during use of the prosthesis in a patient's body. The cross-sectional geometry, the number and the length of the flutes 328 included in the stem section 320 can be adjusted to facilitate resistance to torsional loadings on the hip prosthesis.

The neck section 310 of the femoral component 300 can have a solid cross-section. The stem section 320, however, can have a cross-section that includes both solid and porous components. Solid components of the stem section 320 can be included to withstand fatigue loading in vivo. The porous components of the stem section 320 can be included to reduce flexural rigidity and the weight of the femoral component 300, as well as to induce bone ingrowth, if the outer surface is porous. The combination of both solid and porous components allows the femoral component 300 to be optimized for flexure stiffness to more closely match that of bone and also to minimize stress shielding.

Transitions between the sections 310 and 330 of the femoral component 300 can be optimally included and located in order to avoid high stress zones in the implant and to meet industry standards. The femoral component 300 can be made using additive manufacturing techniques to have a continuous, integrated structure, including either of the two cross-sections 340 and 350, such as those shown and described herein.

FIGS. 3A and 3B include two different exemplary cross-sections 340 and 350, respectively, of the stem section 320 of femoral component 300 taken at 3A-3A in FIG. 3, for example. The stem section 320 in both cross-sections 340 and 350 can have a cross-section having a circular profile, as shown. However, other shapes of an outer perimeter or surface of the cross-section are also contemplated by the disclosure. The stem section 320 can also include a plurality of longitudinally extending flutes 328 which project outwardly from an outer surface of the stem section 320.

The first exemplary cross-section 340 of the stem section 320 of femoral component 300, shown in FIG. 3A, can include a core (or longitudinal chamber or aperture) 342 that is porous. The porous structure can be formed of a metal alloy using additive manufacturing. Alternatively, however, the core 342 can be hollow or of solid construction of an alternative material including but not limited to metal, metal alloy or polymers. The cross-section 340 can include a first circumferential solid portion 344 adjacent the core 342. The core 342, alternatively, can be made of a solid material that is different from the solid portion 344. The solid portion 344 can include a plurality of longitudinally extending flutes 328 as shown.

In another example, the core 342 can be formed from a solid material that is different from the solid material of the solid portion 444, which can have a different mechanical property. For example, the mechanical property of strength of the core 342, if it were a solid portion can be less than that of the solid portion 344. Other examples of mechanical properties that can differ in the second solid portion of the core 342 from the solid portion 344 include, but are not limited to, yield strength, compressive strength, fatigue strength, impact strength, deformation, strain, deflection, elasticity, and plasticity, etc.

The second exemplary cross-section 350 of the stem section 320 of femoral component 300, shown in FIG. 3B, can include a solid portion 354 that includes two longitudinal chambers or apertures 352 that are located side-by-side. The two longitudinal chambers 352 can be porous or, alternatively, can be solid and made of an alternative material, or can be hollow. The solid portion 354 can include a plurality of longitudinally extending flutes 328 as shown. The stem section 320 of femoral component 300 can, alternatively, include a solid distal section that does not include a porous portion.

Prior to hip replacement or revision surgery, a surgeon can use x-ray technology to template, or determine the type and size of implant (or its components) that the surgeon will use. Alternatively, or additionally, during a hip replacement or revision, for example, a surgeon can take a number of measurements to ensure proper prosthesis selection, limb length and hip rotation. After making an incision, the surgeon can gain access to the joint and push the femur out of the socket, thereby exposing the joint cavity. A deteriorated femoral head can be removed and the acetabulum can be prepared by cleaning and enlarging with circular reamers of gradually increasing size. Also, the surgeon may measure the native femoral head once it is excised to determine the size and type of implant to use. In addition, after the joint is dislocated, and as the surgeon is preparing the bone (possibly removing bone) for the implant, the surgeon can determine the size/offset of the implant to be implanted by using trials (or provisional implants) in the joint that represent the implants that are available. The trial or provisional implants are used to check tissue tension, joint stability, range of motion and leg length. A new acetabular shell, which can be metal, can be implanted securely within the prepared hemispherical socket. A plastic inner can be placed within the metal acetabular shell and fixed into place. If the old acetabular shell is sufficient, during a revision surgery, the shell may not be replaced, and only a new liner may be used.

Next, the femur can be prepared to receive a stem of a femoral component. The inside of the femur can include a intramedullary canal that can be cleaned and enlarged by broaches, reamers, and other tools, thereby creating a cavity that is smaller than, but that corresponds to the outer profile of the implant stem. That outer profile or geometry is dictated by the size and shape of the stem and should be prepared so that the stem, upon insertion, can fit tightly and securely in the canal. The stem can be placed in the canal with or without cement. Finally, a femoral ball can be attached to a proximal end of the stem and can be seated within a cup so the joint is properly aligned. The incision can then be closed.

The present disclosure includes a method of manufacturing a femoral component of a prosthetic hip implant, the method comprising: creating a 3D model of the femoral component; and additive manufacturing of the femoral component from the 3D model, wherein the femoral component comprises: a neck portion; and a stem portion that comprises a first solid portion and at least one additional portion including at least one of a hollow portion, a porous portion, and a second solid portion comprised of a different solid material from a solid material of the first solid portion, wherein the first solid portion and the at least one additional portion are in a predetermined configuration. The step of additive manufacturing can, for example, include direct metal laser sintering the femoral component, selective laser sintering the femoral component or electron beam melting the femoral component.

The present disclosure also contemplates use of software to additively manufacture (e.g., 3D print) the femoral component described herein. Thus, the present disclosure contemplates a system comprising: a display that displays a printing template, wherein the printing template describes a femoral component comprising: a neck portion; and a stem portion including a proximal end and a distal end, wherein the neck portion extends from the proximal end, and the stem portion comprises a first solid portion and at least one additional portion, the at least one additional portion including at least one of a hollow portion, a porous portion, or a second solid portion comprised of a different solid material from a solid material of the first solid portion, wherein the first solid portion and the at least one additional portion are in a predetermined configuration; and a module that, in response to a printing template by a user, executes the printing template to generate a geometric representation for use as input to a 3D printer.

Additionally, the present disclosure also contemplates a method comprising: displaying a printing template, wherein the printing template describes a femoral component comprising: a neck portion; and a stem portion including a proximal end and a distal end, wherein the neck portion extends from the proximal end, and the stem portion comprises a first solid portion and at least one additional portion, the at least one additional portion including at least one of a hollow portion, a porous portion, or a second solid portion comprised of a different solid material from a solid material of the first solid portion, wherein the first solid portion and the at least one additional portion are in a predetermined configuration; and executing the printing template to generate a geometric representation for use as input to a 3D printer.

Changes and modifications, additions and deletions may be made to the structures and methods recited above and shown in the drawings without departing from the scope or spirit of the disclosure and the following claims.

Various Notes & Examples

To further illustrate the femoral component of the hip implant, and the methods disclosed herein, the following non-limiting examples are provided:

Example 1 includes a femoral component of a prosthetic hip implant, the femoral component comprising: a neck portion; and a stem portion including a proximal end and a distal end, wherein the neck portion extends from the proximal end, and the stem portion comprises a first solid portion and at least one additional portion, the at least one additional portion including at least one of a hollow portion, a porous portion, or a second solid portion comprised of a different solid material from a solid material of the first solid portion, wherein the first solid portion and the at least one additional portion are in a predetermined configuration; wherein the femoral component comprises a unitary component that is formed by additive manufacturing of the femoral component from a 3D model of the femoral component.

Example 2 includes the femoral component of example 1, wherein the at least one additional portion includes a hollow core extending longitudinally through at least a portion of the stem portion and a porous portion circumscribing the first solid portion, and wherein the first solid portion circumscribes the hollow core.

Example 3 includes the femoral component of example 1, wherein the at least one additional portion includes a porous core extending longitudinally through at least a portion of the stem portion and a second porous portion circumscribing the first solid portion, and wherein the first solid portion circumscribes the porous core.

Example 4 includes the femoral component of any one of examples 1-3, wherein the neck portion is solid and at least a portion of the stem portion located at or near the distal end is solid.

Example 5 includes the femoral component of example 1, wherein the at least one additional portion includes a first aperture and a second aperture that extend longitudinally through at least a portion of the stem portion, wherein the first solid portion surrounds the first and second apertures, and wherein the at least one additional portion further includes a first porous portion circumscribing the first solid portion.

Example 6 includes the femoral component of example 1, wherein the at least one additional portion includes a first porous portion and a second porous portion that extend longitudinally through at least a portion of the stem portion, wherein the first solid portion surrounds the first and second porous portions, and wherein the at least one additional portion further includes a third porous portion circumscribing the first solid portion.

Example 7 includes the femoral component of example 1, wherein the first solid portion comprises an I-beam-shaped solid portion extending longitudinally through at least a portion of the stem portion, wherein the at least one additional portion includes a first porous portion circumscribing the I-beam-shaped solid portion and forming an outer surface of at least a portion of the stem portion, and wherein the at least one additional portion further includes a first aperture and a second aperture that extend longitudinally through at least a portion of the stem portion between the I-beam-shaped solid portion and the first porous portion.

Example 8 includes the femoral component of example 1, wherein the first solid portion comprises an I-beam-shaped solid portion extending longitudinally through at least a portion of the stem portion, wherein the at least one additional portion includes a first porous portion circumscribing the I-beam-shaped solid portion and forming an outer surface of at least a portion of the stem portion, and wherein the at least one additional portion further includes a second porous portion and a third porous portion that extend longitudinally through at least a portion of the stem portion between the I-beam-shaped solid portion and the first porous portion.

Example 9 includes the femoral component of any one of examples 1-8, wherein the stem portion is tapered from the proximal end to the distal end.

Example 10 includes the femoral component of any one of examples 1-9, wherein the stem portion has a cross-sectional profile that is trapezoidal-shaped, rectangular-shaped, oval-shaped, circular-shaped, or teardrop-shaped.

Example 11 includes the femoral component of any one of examples 1-10, wherein the stem portion includes a plurality of longitudinally extending flutes along a length of an outer surface thereof.

Example 12 includes a prosthetic hip implant comprising: a femoral ball; and a femoral component comprising: a neck portion configured to connect to the femoral ball; and a stem portion including a proximal end and a distal end, wherein the neck portion extends from the proximal end, and the stem portion comprises a first solid portion and at least one additional portion including at least one of a hollow portion, a porous portion, and a second solid portion comprised of a different solid material from a solid material of the first solid portion, wherein the first solid portion and the at least one additional portion are in a predetermined configuration; wherein the femoral component comprises a unitary component that is formed by additive manufacturing of the femoral component from a 3D model of the femoral component.

Example 13 includes the prosthetic hip implant of example 12, further comprising an acetabular shell.

Example 14 includes a method of manufacturing a femoral component of a prosthetic hip implant, the method comprising: creating a 3D model of the femoral component; and additive manufacturing of the femoral component from the 3D model, wherein the femoral component comprises a unitary component comprising: a neck portion; and a stem portion including a proximal end and a distal end, wherein the neck portion extends from the proximal end, and the stem portion comprises a first solid portion and at least one additional portion including at least one of a hollow portion, a porous portion, and a second solid portion comprised of a different solid material from a solid material of the first solid portion, wherein the first solid portion and the at least one additional portion are in a predetermined configuration.

Example 15 includes the method of example 14, wherein the step of additive manufacturing includes direct metal laser sintering the femoral component, selective laser sintering the femoral component or electron beam melting the femoral component.

Example 16 includes the method of example 14, wherein the at least one additional portion includes a hollow core extending longitudinally through at least a portion of the stem portion and a porous portion circumscribing the first solid portion, and wherein the first solid portion circumscribes the hollow core.

Example 17 includes the method of example 14, wherein the at least one additional portion includes a porous core extending longitudinally through at least a portion of the stem portion and a second porous portion circumscribing the first solid portion, and wherein the first solid portion circumscribes the porous core.

Example 18 includes the method of any one of examples 14-17, wherein the neck portion is solid and at least a portion of the stem portion located at or near the distal end is solid.

Example 19 includes the method of example 14, wherein the at least one additional portion includes a first aperture and a second aperture that extend longitudinally through at least a portion of the stem portion, wherein the first solid portion surrounds the first and second apertures, and wherein the at least one additional portion further includes a first porous portion circumscribing the first solid portion.

Example 20 includes the method of example 14, wherein the at least one additional portion includes a first porous portion and a second porous portion that extend longitudinally through at least a portion of the stem portion, wherein the first solid portion surrounds the first and second porous portions, and wherein the at least one additional portion further includes a third porous portion circumscribing the first solid portion.

Each of these non-limiting examples can stand on its own, or can be combined in any permutation or combination with any one or more of the other examples.

The above detailed description includes references to the accompanying drawings, which form a part of the detailed description. The drawings show, by way of illustration, specific embodiments in which the present subject matter can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the present subject matter should be determined with reference to the appended claims, along with the full scope of equivalents to which such claims are entitled.

What is claimed is:

1. A femoral component of a prosthetic hip implant, the femoral component comprising:
    a neck portion; and
    a stem portion extending longitudinally from a proximal end to an opposing distal end, wherein the neck portion extends proximally from the proximal end, and the stem portion comprises two distinct longitudinal stem segments including:
    a solid distal segment extending longitudinally from the distal end of the stem portion and terminating at a cross-sectional transition of the stem portion, the solid distal segment comprising a single homogenous material; and
    a hybrid proximal segment extending longitudinally from the cross-sectional transition of the stem portion and terminating at the proximal end of the stem portion, the hybrid proximal segment including an outer porous portion defining an outer surface of the hybrid proximal segment and at least one of a hollow core portion, a porous core portion, or a solid core portion;

wherein the femoral component comprises a unitary component that is formed by additive manufacturing of the femoral component from a 3D model of the femoral component.

2. The femoral component of claim 1, wherein the hybrid proximal segment includes a hollow core portion.

3. The femoral component of claim 1, wherein the hybrid proximal segment includes a porous core portion.

4. The femoral component of claim 1, wherein the neck portion is solid.

5. The femoral component of claim 1, wherein the stem portion is tapered from the proximal end to the distal end.

6. The femoral component of claim 1, wherein the stem portion has a cross-sectional profile that is trapezoidal-shaped or circular-shaped.

7. A prosthetic hip implant comprising:
a femoral ball; and
a femoral component comprising:
   a neck portion configured to connect to the femoral ball; and
   a stem portion including a proximal end and a distal end, wherein the neck portion extends proximally from the proximal end, and the stem portion comprises a solid distal segment at or near the distal end of the stem portion and a hybrid proximal segment at or near the proximal end of the stem portion, the solid distal segment comprising a single homogenous material and including a smooth outer surface, the hybrid proximal segment including an outer porous portion defining an outer surface of the hybrid proximal segment and two or more of a hollow core portion, a porous core portion, or a solid core portion, wherein the outer porous portion is permeated with interconnected interstitial pores structured to promote at least one of bone ongrowth or bone ingrowth;

wherein the femoral component comprises a unitary component that is formed by additive manufacturing of the femoral component from a 3D model of the femoral component.

8. The prosthetic hip implant of claim 7, further comprising an acetabular shell.

9. A femoral component of a prosthetic hip implant, the femoral component comprising:
   a solid proximal section including a neck portion configured to engage a femoral ball;
   a solid distal section including a smooth outer surface; and
   a hybrid middle section disposed between the proximal section and the distal section, the middle section including an inner core portion, a first circumferential portion adjacent to the inner core portion, and a second circumferential porous portion adjacent to the first circumferential portion and defining an outer surface of the middle section, wherein the second circumferential porous portion is permeated with interconnected interstitial pores structured to promote at least one of bone ongrowth or bone ingrowth;
   wherein the inner core portion is a cavity surrounded by an inner circumferential wall of the first circumferential portion;
   wherein the solid proximal section and the solid distal section comprise a single homogenous material; and
   wherein the femoral component comprises a unitary component that is formed by additive manufacturing from a 3D model of the femoral component.

10. The femoral component of claim 9, wherein the first circumferential portion comprises a first circumferential porous portion formed from a porous material around the cavity.

11. The femoral component of claim 9, wherein the first circumferential portion comprises a first circumferential solid portion formed from a solid material around the cavity.

* * * * *